(12) United States Patent
Pellecchia

(10) Patent No.: US 7,723,076 B2
(45) Date of Patent: May 25, 2010

(54) USE OF SELECTIVE LABELING TO DETECT AND CHARACTERIZE MOLECULAR INTERACTIONS BY NUCLEAR MAGNETIC RESONANCE SPECTROSCOPY

(75) Inventor: Maurizio Pellecchia, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 823 days.

(21) Appl. No.: 11/504,133

(22) Filed: Aug. 14, 2006

(65) Prior Publication Data

US 2006/0275876 A1    Dec. 7, 2006

Related U.S. Application Data

(62) Division of application No. 10/686,192, filed on Oct. 15, 2003, now abandoned.

(60) Provisional application No. 60/422,638, filed on Oct. 29, 2002.

(51) Int. Cl.
  C12P 21/02  (2006.01)
  C12P 13/04  (2006.01)
  C12P 13/22  (2006.01)
  C12P 13/10  (2006.01)
(52) U.S. Cl. .................... 435/71.2; 435/70.1; 435/69.1; 435/106; 435/108; 435/114
(58) Field of Classification Search .................... None
  See application file for complete search history.

(56) References Cited

U.S. PATENT DOCUMENTS

| 5,698,401 A | 12/1997 | Fesik et al. |
| 5,804,390 A | 9/1998 | Fesik et al. |
| 2001/0004528 A1* | 6/2001 | Fesik et al. .................. 435/7.1 |

OTHER PUBLICATIONS

Rodriguez-Mias, R. et al., "Use of Selective Trp Side Chain Labeling to Characterize Protein-Protein and Protein-Ligand Interactions by NMR Spectroscopy", 2003, J. Am. Chem. Soc., vol. 125: pp. 2892-2893.*
Gardner, K. et al., "Production and Incorporation of 15N, 13C, 2H (1H-delta1 Methyl) Isoleucine into Proteins for Multidimensional NMR studies", 1997, J. Am. Chem. Soc., vol. 119: pp. 7599-7600.*
Goto, N. et al "New Developments in isotope labeling strategies for protein solution NMR spectroscopy", 2000, Cur. Opin. Struct. Biol., vol. 10: pp. 585-592.*
Rosen, M. et al., "Selective Methyl Group Protonation of Perdeuterated Proteins", 1996, J> Mol. Biol., vol. 263: pp. 627-636.*
Altschl et al. "Gapped Blast and PSI-Blast: a new generation of protein database search programs." *Nucleic Acids Res.* 25:3389-3402 (1997).
Bogan and Thorn. "Anatomy of Hot Spots in Protein Interfaces." *J. Mol Biol.* 280:1-9 (1998).
Crawford. "Synthesis of Tryptophan from Chorismate: Comparative Aspects." *Methods in Enzymology.* 142:293-300 (1987).
Eddy. "Profile hidden Markov models." *Bioinformatics.* 14:755-763 (1998).
Fildes. "The Biosynthesis of Tryptophan by Bact. Typhosum." *Br. J. Exp. Pathol.* 26:416-428 (1945).
Gribskov et al. "Profile Analysis." *Methods in Enzymology.* 183:146-159 (1990).
Hibler et al. Isotopic labeling with hydrogen-2 and carbon-13 to compare conformations of proteins and mutants generated by site-directed mutagenesis. *Methods in Enzymology.* 177:74-86 (1989).
Kay and Gardner. "Solution NMR spectroscopy beyond 25 kDa." *Curr. Op. Struct. Biol.* 7:722-731 (1997.).
Kim et al. "The specific incorporation of labeled aromatic amino acids into proteins through growth of bacteria in the presence of glyphosate." *FEBS.* 272:34-36 (1990).
Lemaster. "Deuteration in protein proton magnetic resonance." *Methods in Enzymology.* 177:23-43 (1989).
Lichtarge and Sowa. "Evolutionary predictions of binding surfaces and interactions." *Curr. Opin. Struct. Biol.* 12:21-27 (2002).
Minks et al. "Atomic mutations at the single tryptophan residue of human recombinant annexin v: effects on structure, stability, and activity." *Biochemistry.* 38:10649-10659 (1999).
Muchmore et al. "Expression and nitrogen-15 labeling of proteins for proton and nitrogen-15 nuclear magnetic resonance." *Methods in Enzymology.* 177:44-73 (1989).
Pellecchia et al. "NMR-based structural characterization of large protein-ligand interactions." *Journal of Biomolecular NMR.* 22:165-173 (2002).
Pellecchia et al. "NMR in Drug Discovery." *Nature Rev. Drug Disc.* 1:211-219 (2002).
Pervushin et al. "Attenuated $T_2$ relaxation by mutual cancellation of dipole-dipole coupling and chemical shift anisotropy indicates an avenue to NMR structures of very large biological macromolecules in solution." *Proc. Natl. Acad. Sci. USA.* 94:12366-12371 (1997).
Sixl et al. "F-n.m.r. studies of ligand binding to 5-fluorotryptophan- and 3-fluorotyrosine-containing cyclic AMP receptor protein from *Escherichia coli.*" *Biochem. J.* 266:545-552 (1990).
Sun et al. "NMR Structure and Mutagenesis of the Third Bir Domain of the Inhibitor of Apoptosis Protein XIAP." *J. Biol. Chem.* 275:33777-33781 (2000).
Wüthrich. "The second decade—into the third millennium." *Nat. Struct. Biol.* 5:492-495 (1998).

* cited by examiner

*Primary Examiner*—Michael Burkhart
(74) *Attorney, Agent, or Firm*—Knobbe Martens Olson & Bear LLP

(57) ABSTRACT

Methods of detecting interactions of a putative ligand with a selectively labeled target molecule, methods of screening for compounds which bind to a selectively labeled target molecule, methods for calculating the dissociation constant of a ligand that binds to a selectively labeled target molecule, and methods to determine the specific amino acids of a target molecule affected by the binding of a ligand, as well as compounds identified by these screening methods, are provided.

24 Claims, 1 Drawing Sheet

USE OF SELECTIVE LABELING TO DETECT AND CHARACTERIZE MOLECULAR INTERACTIONS BY NUCLEAR MAGNETIC RESONANCE SPECTROSCOPY

PRIORITY CLAIM

This application is a divisional of U.S. application Ser. No. 10/686,192, filed Oct. 15, 2003 now abandoned, which claims priority under 35 U.S.C. §119(e) to U.S. Provisional Application No. 60/422,638, filed Oct. 29, 2002, both of which are hereby expressly incorporated herein by reference in their entirety.

BACKGROUND OF THE INVENTION

1. Field of the Invention

The present invention relates to selectively labeled molecules and the use of nuclear magnetic resonance spectroscopy to detect and characterize molecular interactions between the selectively labeled molecules and putative ligands.

2. Background of the Invention

Random screening of synthetic and natural product libraries to discover compounds that bind to a particular target molecule is a common method for obtaining new pharmaceutical entities. A target molecule is typically exposed to one or more compounds and assays are performed to determine if complexes between the target molecule and one or more of the compounds are formed. Once random screening has identified a potential candidate, or lead compound, analogs of the lead compound are synthesized in an effort to improve binding and selectivity. The analogs are then screened, usually by the same assays used to identify the lead compound.

A common problem associated with current screening methods involves non-specific ligand binding; that is, the ligand attaches to the target molecule but in a non-specific manner. Such non-specific binding often occurs and is difficult to detect. In such cases, optimization of ligand binding is greatly complicated. The full potential for developing pharmaceutical-based therapies depends not only on screening vast numbers of compounds against a target, but also on determining specific details concerning interactions between the ligand and the target molecule.

Nuclear magnetic resonance (NMR) spectroscopy is known for its ability to characterize macromolecular structures, and is a technique for investigating both static and transient features of ligand binding to a target molecule (Pellecchia, et al., *Nature Rev Drug Disc* 2002, 1:211). NMR spectroscopy is a useful tool for determining the binding of ligands to target molecules, and has the advantage of being able to detect and quantify interactions with high sensitivity without requiring prior knowledge of protein function. Furthermore, NMR spectroscopy can provide structural information on both the target and the ligand to aid subsequent optimization of weak-binding hits into high-affinity leads.

Methods of detecting binding of a ligand compound to a target biomolecule by generating first and second nuclear magnetic resonance correlation spectra from target biomolecules which have been uniformly labeled are reported in U.S. Pat. Nos. 5,698,401 and 5,804,390. The first spectrum is generated from data collected on the target substance in the absence of ligands, and the second in the presence of one or more ligands. A comparison of the two spectra permits determination of which compounds in the mixture of putative ligands bind(s) to the target biomolecule.

Despite the broad applicability of using NMR spectroscopy to determine molecular interactions, its use with macromolecules is complicated by the extremely complex spectra associated with macromolecules. Although, isotope labeling in macromolecular NMR spectroscopy can result in increased sensitivity and resolution and in reduced complexity of the NMR spectra, attempts to improve NMR analysis of macromolecules by labeling target molecules with NMR active isotopes has been only marginally successful. Isotope labeling would promote the efficient use of heteronuclear multi-dimensional NMR experiments and provided alternative approaches to the spectral assignment process and additional structural constraints from spin-spin coupling.

Current methods of assessing molecular interaction that utilize NMR spectroscopy typically rely on uniform labeling of the target molecule. When using uniform labeled target molecules, a complete $^1$H and $^{15}$N resonance assignment of at least the backbone nuclei of the target molecule must be completed before any ligand-protein interactions can be assessed by NMR spectroscopy. The assignments are then used to map the interactions of a ligand by following chemical shift changes upon complexation. This process can be quite lengthy and is generally limited to small-to-medium-sized proteins due to line broadening and spectral overlap with larger proteins. Even with the advent of TROSY (Transverse Relaxation Optimized SpectroscopY) (Pervushin, et al., *Proc Natl Aca. Sci USA* 1997, 94:12366; Wüthrich, *Nat Struct Biol* 1998, 5:492) and perdeuteration, the problem of complete resonance assignments in target molecules remains a major stumbling block for NMR ligand-binding studies.

There have been attempts to overcome the problems associated with uniform labeling of target molecules by attempting to selectively label the methyl groups of the amino acids isoleucine, methionine, threonine, alanine, leucine, and valine. However, these amino acids often are present in the interior of the protein and are not involved in ligand or protein binding.

Thus, there is a need for methods for determining molecular interactions by NMR spectroscopy that result in a simplification of the spectrum and enable the study of significantly larger macromolecules. Also needed are improved methods for high-throughput screening using NMR spectroscopy.

SUMMARY OF THE INVENTION

This invention provides selectively labeled molecules and methods for producing these selectively labeled molecules. Also provided is a method for detecting ligand interaction with a target molecule. The selectively labeled molecules of the invention are exposed to one or more putative ligands and examined by NMR spectroscopy. The methods disclosed herein efficiently detect ligand binding to the labeled target molecule.

Also provided are methods to determine the dissociation constant for the ligand-molecule complex. In addition, the methods described herein provide structural information concerning protein-molecule interactions that can be used to guide the optimization of the binding of a ligand. Also provided are methods for high-throughput screening using the selectively labeled molecules of the invention.

In one embodiment of the invention, novel methods are provided for selectively labeling polypeptides by incorporation of $^1$H, $^{13}$C, $^{15}$N and/or $^{19}$F into the side chain of one or more amino acid residues.

The methods described herein allow studies of protein-protein interactions and protein-ligand interactions that are relevant to drug-design and discovery. In addition, the methods can be used to characterize the binding properties of proteins with unknown function.

DETAILED DESCRIPTION OF THE PREFERRED EMBODIMENT

Figure 1:
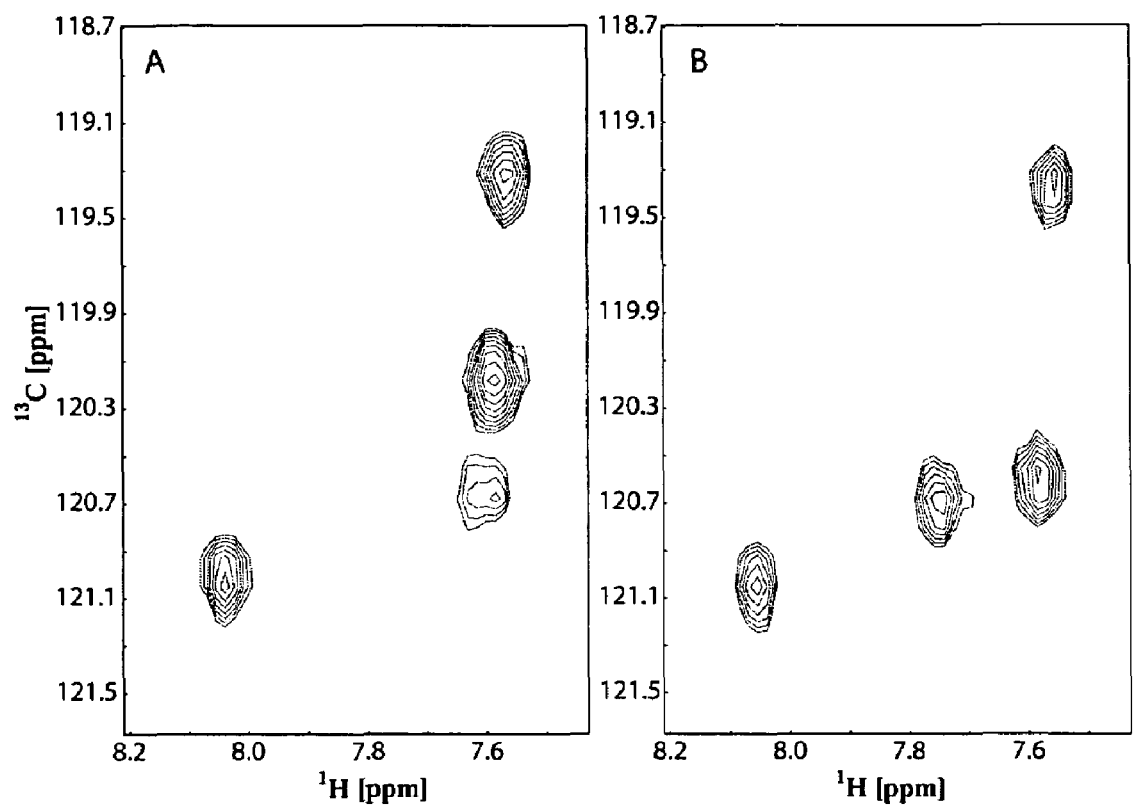
FIG. 1A. The 2D $^{13}C,^{1}H$-HMQC spectra of [4-$^{13}$C]-Tryptophan labeled inhibitor of apoptosis (IAP) third BIR domain (BIR3) non-bound (apo).
FIG. 1B. The 2D $^{13}C,^{1}H$-HMQC spectra of [4-$^{13}$C]-Tryptophan labeled inhibitor of apoptosis (IAP) third BIR domain (BIR3) complexed with an inhibitor peptide AVPI.

Described herein are methods for selectively incorporating labels into target molecules that are useful for examining molecular interactions between the selectively labeled target molecules and putative ligands. Selective labeling permits studies with larger target molecules due to a lowered degree of complexity in the NMR spectra. In addition, selective labeling provides target molecules that are labeled in a manner previously unobtainable. The selective labeling disclosed herein enhances the results of NMR experiments, in particular NMR experiments such as NOE and TROSY experiments.

Target molecules are any molecule capable of examination by NMR spectroscopy. Target molecules can be biomolecules or portions of biomolecules. Examples include lipoproteins, lipoprotein fragments, glycoproteins, glycoprotein fragments, proteins, protein fragments, and polypeptides. The terms protein and polypeptide are interchangeable terms. The term "protein" refers to native polypeptide structures and to fragments of the native structures. The term "polypeptide" includes native protein structures. Target molecules are preferably native protein structures, with or without post-translational modification. More preferred as target molecules are native protein structures that are post-translationally modified.

Selective labeling is defined as labeling substantially every occurrence of at least one particular amino acid throughout a polypeptide sequence. Preferably, at least about 50% of the particular amino acid or amino acids are labeled throughout the polypeptide sequence. More preferably, at least about 75%, or at least about 90% of the particular amino acid or amino acids are labeled throughout the polypeptide sequence. Most preferably, substantially each occurrence of the particular amino acid or amino acids are labeled throughout the polypeptide sequence. Where there is more than one occurrence of an amino acid that is selectively labeled in a target molecule, each labeled amino acid side chain is preferably labeled identically.

Ligands are any composition that may interact with a target molecule. Ligands include substrates, such as enzyme substrates, agonists, antagonists, mixed agonists or antagonist, any biomolecule such as a polypeptide, protein, carbohydrate, lipid, and the like. The ligand can be naturally occurring or synthetic.

The particular amino acid or amino acids to be labeled are preferably those located at a functional site of a polypeptide. A functional site is involved in ligand interaction, catalytic activity, conformational switches, and/or protein-protein interactions. Alternatively, the functional site is a cluster of amino acids whose structural, dynamic and physiochemical properties directly impact ligand interaction and/or transformation. Functional sites are often found on protein surfaces or at protein active sites. The residues involved in functional sites are especially likely to form binding sites and/or active sites and are good choices for selective labeling.

Since functional sites undergo fewer mutations during evolution than other parts of a protein, functional sites can be determined by identifying sequence conservation patterns. This can be done by profile analysis (Gribskov et al., *Methods Enzymol* 1990, 183:146), hidden Markov models (Eddy, *Bioinformatics* 1998, 14:755), by BLAST, such as PSI-BLAST (Altschl et al., *Nucleic Acids Res* 1997, 25:3389), or by evolutionary tracing (Lichtarge and Sowa, *Curr Opin Struct Biol* 2002, 12:21). These methods also indicate putative functions of the proteins.

Preferred amino acids for selective labeling are tryptophan, arginine and tyrosine. Also preferred are aromatic amino acids, i.e., phenylalanine, tyrosine, and tryptophan. A most preferred amino acid for selective labeling is tryptophan because tryptophan side chains are often found at protein binding sites or hot sites and rarely occur in the protein interior.

Selectively labeled molecules, preferably selectively labeled polypeptides, can be exposed to a second molecule and any molecular interaction can be examined by NMR spectroscopy. For example, 2D $^{13}C,^{1}H$-HMQC (heteronuclear multiple quantum coherence) and $^{13}$C-edited $^{1}H,^{1}H$-NOESY NMR experiments can be used to detect molecular interaction and to determine the dissociation constant for any complex. In addition, a predictive model can be created based on the three-dimensional structure of the target and from the relative position of the ligand with respect to the labeled side chain. The use of several different labeled side-chains in a single, selectively-labeled, target-molecule will improve the resolution as well as the predictive nature of the model.

Three amino acids that are commonly found at functional areas of proteins are the two aromatic residues tryptophan and tyrosine and the positively charged amino acid arginine. Among these, tryptophan residues are known to be the most frequently occurring amino acid at protein binding sites (Bogan and Thorn, *J. Mol Biol* 1998, 280:1). These amino acids are capable of making multiple types of favorable interactions that are preferred in the lowered effective dielectric environment of hot spots. Tryptophan, for example, can contribute aromatic π-interactions, a hydrogen-bonding donor, and a large hydrophobic surface. Previous thermodynamic and computational studies have also pointed to the important energetic role of aromatic contacts, and of tryptophan in particular, in generating the exceptional binding free energy of streptavidin-biotin association. Crystallographic characterization of single site tryptophan mutants indicate that several tryptophan residues (Trp79, Trp92, Trp108 and Trp120) play an important role in the hydrophobic binding contributions in streptavidin-biotin interactions. Thus, one aspect of the invention is the selective labeling of tryptophan side chains in a target molecule and NMR spectrographic evaluation of the target molecule with putative ligands. Because of the pivotal role of tryptophan side chains in protein-protein and protein-ligand interactions, selective observation of the NMR signals from these residues provides clear and specific information concerning intermolecular interactions.

In one embodiment of the invention, a labeling scheme is provided that incorporates one or more labels into selected amino acid side chains of a target molecule. For example, a method for $^{13}$C-labeling one or more of the carbon atoms of a side chain of an amino acid residue, and incorporation of the labeled residue in to an otherwise $^{12}$C-labeled target molecule is provided. In addition, a method for $^{1}$H-labeling of one or more atoms in a side chain of an amino acid residue and incorporation of the labeled residue in to an otherwise $^{2}$H-labeled target molecule is provided. In addition, a method for $^{19}$F-labeling of a side chain of an amino acid residue and incorporation of the labeled residue in to a polypeptide is provided. In a particular embodiment, the invention provides [4-$^{13}$C] and/or [2-$^{13}$C] nuclei in tryptophan side-chains in an otherwise $^{12}$C-labeled target molecule. In another embodiment of the invention the selective incorporation of $^{19}$F in tryptophan side chains at positions 5 or 6 of a target molecule is also provided. By similar methods, other nuclei, such as $^{15}N$, can also be incorporated.

Thus, an efficient and cost-effective method for selective incorporation of labeled amino acid residues into target molecules is provided. Preferred labels are atoms having unpaired nuclear spins. Examples of such atoms are $^1H$, $^{13}C$, $^{15}N$, $^{19}F$, $^{31}P$. Target molecules are preferably labeled with $^1H$, $^{13}C$, $^{15}N$, $^{19}F$. More preferred, the target molecules are selectively labeled with $^1H$, $^{13}C$, or $^{19}F$, and any combination of $^{19}F$, $^1H$ and/or $^{13}C$.

Scheme 1.
Chemical structure of tryptophan.
(Numbering according the IUPAC nomenclature).

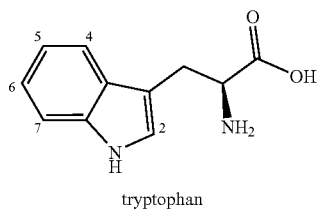

tryptophan

Selective incorporation of amino acid residues into polypeptides, for example recombinant proteins expressed in bacteria, preferably *Escherichia coli*, can be achieved by employing the appropriate growth media (minimal media) supplemented with the desired labeled amino acid(s) (Kay and Gardner, *Curr Op Struct Biol*, 1997, 7:722). Most of the 20 natural amino acids are commercially available with different isotope compositions, obtained by chemical synthesis or purified from labeled algae extracts. Common commercial suppliers include Cambridge stable isotopes, Spectra Stable Isotopes, and ISOTEC-Sigma. Alternatively, the appropriate growth media can be supplemented with the appropriate labeled precursors of the given amino acid, based on the biosynthetic pathways of the given amino acid. For applications in ligand binding studies and drug-discovery, the method of choice depends on several factors such as the degree of incorporation of the selective label, the degree of scrambling of the wanted labels into other amino acids or positions, and the ability to obtain desired amounts of selectively labeled protein in a cost-effective manner.

Means for preparing expression vectors that contain polynucleotide sequences coding specific polypeptides and for transforming host cells with those vectors are well known in the art. (See, for example, Old et al., "Techniques of Gene Manipulation," Blackwell Science, London, 1994, and similar treatises in the field). Likewise, methods for culturing the transformed cells to express the coded polypeptide and for isolating, purifying and re-folding the polypeptide are also well known in the art.

The shikimic acid pathway is the key metabolic pathway in the biosynthesis of the aromatic amino acids—tyrosine, phenylalanine, and tryptophan—which occurs in bacteria. The initial step of the pathway is the condensation of erythrose-4-phosphate (from the pentose phosphate pathway) and phosphoenolpyruvate (from glycolysis). The product of the condensation reaction is then cyclized and reduced to form the intermediate compound shikimate, with the phenolic ring structure characteristic of the aromatic amino acids. Combination of shikimate with an additional molecule of phosphoenolpyruvate produces chorismate, from which alternative pathways lead to either phenylalanine/tyrosine or to tryptophan.

The biosynthesis of tryptophan from chorismate involves four intermediates: anthranilate, ribosylanthranilate, 1'-(O-carboxyphenylamino)-1'-deoxyribulose-5-phosphate, and indoleglycerol phosphate. The biosynthesis occurs via two interconnected pathways that lead to indole (and/or indole-3-glycerolphosphate) that are readily converted into tryptophan via the enzyme tryptophan-syntase (Crawford, *Meth Enz* 1987, 142:293). In the last step of the pathway serine serves as the donor of the α-carbon amino group of tryptophan (Scheme 2).

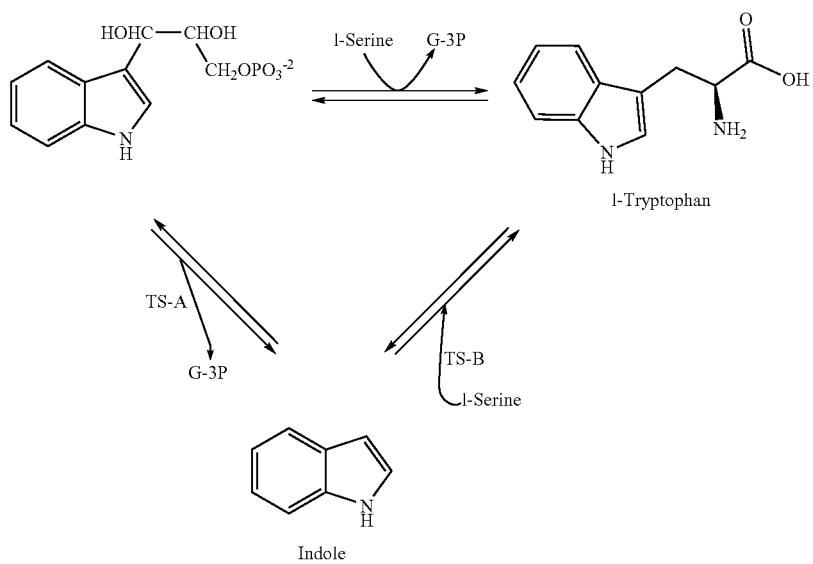

The biosynthesis of tyrosine from chorismate takes place by two alternative routes. The first intermediate in both routes is prephenate, which is converted to either 4-hydroxyphenylpyruvate or arogenate. Tyrosine is then produced from each of these intermediates. The biosynthesis of phenylalanine from chorismate also takes place by two alternative routes. The first intermediate in both routes is also prephenate, which is converted to either phenylpyruvate or the common intermediate arogenate. Phenylalanine is then produced from each of these intermediates.

In one embodiment, labeled indole is added to a recombinant bacteria, engineered to express a target molecule of interest, prior to induction of protein expression. A target molecule is then produced having all its tryptophan residues labeled. Similarly, labeled 4-hydroxyphenylpyruvate or labeled phenylpyruvate can be added to a recombinant bacteria, engineered to express a target molecule of interest, prior to induction of protein expression. The target molecule is then produced having its tyrosine or phenylalanine residues labeled. When one or more labels are incorporated into one or more positions of indole, 4-hydroxyphenylpyruvate, or phenylpyruvate the resulting target molecules have substantially all of the corresponding amino acid side chains labeled. When $^1H$ is selectively incorporated into the target molecule, the recombinant bacteria engineered to express a target molecule of interest is grown on media containing $^2H$ prior to induction of protein expression.

The methods of the invention are exemplified with aromatic amino acids, but the methods can be adapted to the other amino acids based on the biosynthetic pathways of the given amino acid. For example, when selectively labeling aromatic amino acids, labeled precursors and specific inhibitors of the particular amino acid are used. Likewise, when selectively labeling non-aromatic amino acids, labeled precursors and specific inhibitors of the particular amino acid are used. For example, arginine is synthesized by bacteria from glutamate. Thus, adding a labeled arginine precusor, such as ornithine, citrulline, or argininosuccinate, and a selective inhibitor of one of these steps to a recombinant bacteria, engineered to express a target molecule of interest, prior to induction of protein expression, will produce a target molecule having its arginine residues labeled. Alternatively, labeled arginine and a similarly labeled arginine precursor can be added to a recombinant bacteria engineered to express a target molecule of interest to produce a selectively labeled target molecule.

Selectively labeled target molecules produce greatly simplified NMR spectra. Moreover, selective $^{13}C$ labeling of target molecules has the additional advantage of permitting use of the aromatic-TROSY effect that is optimal at magnetic fields corresponding to 600 MHz $^1H$ frequency (Pervushin et al., *Proc Natl Acad Sci USA* 1997, 94:12366). Selective $^1H$ labeling is particularly useful in larger target molecules, as the deleterious $^1H$-$^1H$ dipole-dipole interactions will be mostly replaced by the less efficient $^2H$-$^1H$ dipole-dipole interactions. Elimination of the $^1H$-$^1H$ dipole-dipole interactions enables the study of very large target molecules by NMR spectroscopy. In addition, measurements of intermolecular distances in complexes by nuclear Overhauser effects (NOEs) can be readily obtained using the selectively $^1H$-labeled target molecules. In addition, 2D $^1H$,$^1H$ NOESY and/or $^{13}C$-resolved (or edited) $^1H$,$^1H$ NOESY pulse sequences can be used to determine intermolecular distances using the selectively $^1H$-labeled target molecules.

In one embodiment, the invention provides an efficient and cost-effective method for incorporation of 2-$^{13}C$-tryptophan and/or 4-$^{13}C$-tryptophan in to target molecules. Details of the method are provided below in Example 1. The method uses 2-$^{13}C$ indole and/or 4-$^{13}C$ indole as precursors for tryptophan synthesis in bacteria, preferably in *Escherichia coli*. The labeled indole precursors are commercially available from suppliers such as Cambridge Isotopes Laboratories.

Example 1

*Escherichia coli* strains comprising an inducible vector for a given protein were grown in minimal growth media containing $^{12}C$-, $^1H$-glucose as the sole carbon source in addition to salts and other nutrients in amounts necessary for bacterial growth prior to induction. Once the bacteria reached an acceptable mass, measured, for example, in terms of optical density at 600 nm of the growth media ($OD_{600}$), protein expression was induced. At this point, the bacterial growth is minimal and the metabolism of the bacteria is shifted towards the biosynthesis of proteins and consequently of amino acids. Addition of small amounts of 2-$^{13}C$-indole or 4-$^{13}C$-indole to the growth media resulted in efficient transformation of these precursors into labeled tryptophan, via the tryptophan-synthase pathway, which was incorporated into various target molecules. Because indole can be transformed into tryptophan in a single step by the bacteria, and because of its unique chemical structure, being quite distinct form any other common metabolite, there was no scrambling of the label in the target molecule when various labeled indoles were used as precursors.

Example 2

In an additional embodiment of the invention, selective $^1H$ labeling of tryptophan side chains (with or without $^{13}C$ labeling) was achieved by perdeuteration of the target molecule by replacing water with $^2H_2O$ in the growth media, and supplementing indole (or $^{13}C$-indole) to the media to obtain a target molecule that is uniformly $^2H$-labeled with the exception of selectively $^1H$-labeled tryptophan side chains. This selective $^1H$-tryptophan labeling is particularly useful in larger proteins, as the deleterious $^1H$-$^1H$ dipole-dipole interactions will be mostly replaced by the less efficient $^2H$-$^1H$-tryptophan dipole-dipole interactions. Elimination of the $^1H$-$^1H$ dipole-dipole interactions enables the study of very large proteins and/or protein complexes by NMR spectroscopy. In addition, measurements of $^1H$-tryptophan—ligand distances in complexes via $^1H$-tryptophan/$^1H$-ligand NOEs can be readily obtained by using the selectively $^1H$-labeled target molecules. In addition, 2D $^1H$,$^1H$ NOESY and/or $^{13}C$-resolved (or edited) $^1H$,$^1H$ NOESY pulse sequences can be used to determine intermolecular distances by using the selectively $^1H$-labeled target molecules.

Example 3

The incorporation of $^{19}F$-labeled amino acids into target molecules has been reported. For example, supplementation of growth media with the $^{19}F$-labeled amino acids has been reported. However, not only was the level of $^{19}F$ incorporation was too low to be useful, the location of the $^{19}F$ nucleus in the aromatic amino acid was not uniform (Sixl et al., *Biochem J* 1990, 266:545). Simple supplementation of growth media with the $^{19}F$-labeled amino acids suffers from the additional problem that $^{19}F$-tryptophan is toxic to strains that are wild-type with respect to tryptophan biosynthesis.

Another reported method attempted to incorporate $^{19}F$-labeled aromatic amino acids into target molecules by blocking tryptophan biosynthesis with glyphosate, which is an inhibitor of the 3-enolpyruvyl-shikimate-5-phosphate synthase reaction of aromatic amino acid biosynthesis (Kim et al., *FEBS* 1990, 272:34). Glyphosate, however, completely inhibits the entire synthetic pathway for all aromatic amino acids, so that these need to supplemented to the media as well to ensure bacterial growth.

Another embodiment of this invention provides several methods to efficiently incorporate $^{19}$F-labeled amino acids into polypeptides. In one embodiment of the invention the tryptophan residues of a polypeptide are $^{19}$F labeled. For example, recombinant bacteria engineered to express a target molecule were incubated with $^{19}$F-tryptophan and indoleacrylic acid, an inhibitor of tryptophan-synthase. Indoleacrylic acid is quite similar to tryptophan and earlier reports on the antibiotic properties of this compound on certain bacterial strains were attributed to the inhibition of biosynthesis of tryptophan, as accumulation of indole was detected (Fildel, *Br J Exp Pathol* 1945, 26:416). In another embodiment of the invention, recombinant bacteria engineered to express a target molecule were incubated with $^{19}$F-tryptophan, $^{19}$F-indole (with the same fluorinated position as $^{19}$F-tryptophan) and serine. In this way, biosynthesis of tryptophan is either inhibited by $^{19}$F-indole or results in synthesis of additional $^{19}$F-tryptophan. Similarly, tryptophan with other labels, such as $^{1}$H, $^{15}$N, $^{13}$C, can be incorporated into a selectively labeled target molecule.

Example 4

Programmed cell death, or apoptosis, occurs naturally during the development and maintenance of animal tissues and organs. During these processes more cells are produced than are required for building tissues and organs. The unwanted cells are programmed to die, either because the chemical signals that direct them to go on living are suppressed or because they receive a specific signal to die. Suppression of apoptosis is associated with a variety of diseases such as neurodegenerative disorders and the uncontrolled cell growth in leukemia and other cancers.

One class of proteins that negatively regulates cell death signaling is the inhibitor of apoptosis proteins (IAPs). Members of this family are characterized by having one or more baculovirus IAP repeats called BIR domains, which consist of approximately 70 amino acids that contain the characteristic signature sequence $CX_2CX_{16}HX_6C$.

IAPs are known to bind to and inhibit the cysteine proteases known as caspases, which play a key role in the execution of programmed cell death. Caspase inhibition by the IAPs can directly explain their antiapoptotic activities. Human X-linked inhibitor of apoptosis protein (XIAP) inhibits caspase-9. The BIR3 domain of XIAP is responsible for the potent inhibition of caspase-9. Of the approximately 70 amino acids of the BIR3 domain, only Glu-314, Trp-310, and His-343 have been shown to have a large effect on caspase-9 inhibition (Sun et al., *J Biol Chem* 2000, 275:33777).

Selectively labeled BIR3 was prepared according to the methods of this invention. In particular, 5-$^{19}$F-tryptophan-labeled BIR3 and 6-$^{19}$F-tryptophan-labeled BIR3 were prepared by the methods described herein. The fluorinated analogs 5-$^{19}$F-tryptophan and 6-$^{19}$F-tryptophan are commercially available from Sigma. One-dimensional $^{19}$F NMR spectra of 5-$^{19}$F-tryptophan BIR3 reveals the presence of fours peaks, one for each tryptophan in the sequence. The yields of $^{19}$F incorporation into the target compounds were compared by using mass spectrometry. The results from these experiments showed that the use of indoleacrylic acid results in higher $^{19}$F incorporation for the four tryptophan residues in BIR3. In fact the incorporation was nearly 100% efficient.

Fluorinated analogues of aromatic amino acids are particularly useful because the variations in chemical shift of the fluorine residues are sufficiently large to permit identification of individual resonances, even in relatively large proteins. Additional advantages resulting from use of the $^{19}$F nucleus are that $^{19}$F occurs in 100% natural abundance and the sensitivity is close to that for the proton.

FIG. 1 shows a two-dimensional $^{13}$C,$^{1}$H HMQC spectra recorded on a Varian Unity+ 500 spectrometer with a 100 μM sample of 4-$^{13}$C-tryptophan labeled BIR3 domain. Four tryptophan residues are present in the sequence of the protein. The asterisk in FIG. 1B indicates the tryptophan residue involved in interaction with smac N-terminal tetrapeptide region.

The selectively labeled 5-$^{19}$F-tryptophan and/or 6-$^{19}$F-tryptophan target molecules are utilized in 1D $^{19}$F NMR and heteronuclear $^{19}$F,$^{1}$H-NOESY NMR experiments to analyze ligand interactions such as ligand binding. The selectively labeled target molecules are also utilized to determine the dissociation constant for target molecule-ligand complexes, and to provide models based on the three-dimensional structure of the target and the relative position of the ligand with respect to labeled side-chain(s). These experiments are quite sensitive because of the high magnetic susceptibility of $^{19}$F.

Example 5

The dissociation constant, KD, for a given ligand and its target molecule can be determined by generating a first NMR spectrum of a specifically labeled target molecule; exposing the target molecule to various concentrations of a ligand; generating a NMR spectrum at each concentration of ligand employed; comparing the spectra generated to the first spectrum of the target molecule; and calculating the dissociation constant between the target molecule and the ligand from those differences.

The screening method can be used to determine the dissociation constant of one ligand of the target molecule in the presence of a second molecule. The process of determining the dissociation constant of a ligand in the presence of a second bound ligand is performed by mixing the selectively labeled target molecule to a ligand before exposing the target molecule to the test compounds. The screening method is additionally able to provide information regarding the binding of a second or subsequent ligand to the target molecule. This second ligand may be chemically linked to the first ligand bound to the target molecule, thus providing a new composite molecule for use in affecting the target molecule.

In one embodiment of the invention, the selectively labeled target molecules are used in high-throughput screening. For example, a plurality of putative ligands are exposed sequentially or simultaneously to a selectively labeled target molecule. In another embodiment, a ligand is exposed to a plurality of selectively labeled target molecules, either sequentially or simultaneously. In another embodiment, a plurality of ligands are exposed to a plurality of labeled target molecules. In cases where a plurality of labeled target molecules are used, it is preferred to use targets with substantially non-overlapping spectra.

When more than one compound is screened for binding to a target molecule, for example a mixture or a library of compounds, and where a difference arises between the first spectrum generated from the target molecule alone and that generated from the target molecule in the presence of compound(s), additional steps are performed to identify which specific compound or compounds contained in the mixture is actually binding to the target molecule. Those additional steps include exposing the target molecule individually to each compound of the mixture; generating a NMR spectrum of the labeled target molecule that has been individually exposed to each compound; and comparing each spectrum to the first spectrum generated from the target molecule alone to determine differences in any of those compared spectra. The differences in the spectra facilitate the identification of a compound that is a ligand.

In one embodiment of the invention, an orphan gene is cloned and its corresponding protein is selectively labeled. Based on sequence homology data, ligands are selected and screened for interaction. Positive interaction between the ligand and protein validates the sequence homology analysis, while negative interactions invalidate the sequence homology analysis.

While the present invention has been described in some detail for purposes of clarity and understanding, one skilled in the art will appreciate that various changes in form and detail can be made without departing form the true scope of the invention. All figures, tables, and appendices, as well as patents, applications, and publications, referred to above, are hereby incorporated by reference in their entireties.

What is claimed is:

1. A method, for producing a target molecule wherein substantially every occurrence of a particular amino acid in the target molecule is labeled, wherein the amino acid is located at a functional site of the target molecule; and wherein substantially all occurrences of other amino acids are unlabeled, the method comprising:
    providing a labeled precursor that selectively labels only the particular amino acid; and
    culturing a transformed cell line containing an expression vector comprising a polynucleotide encoding the target molecule in a medium comprising a labeled precursor to biosynthesis of the amino acid.

2. The method of claim 1, wherein the amino acid is tryptophan.

3. The method of claim 1, wherein the amino acid is arginine, tyrosine, or phenylalanine.

4. The method of claim 1, wherein the amino acid is labeled with a nucleus selected from the group consisting of $^1$H, $^{13}$C, $^{15}$N, and $^{19}$F.

5. The method of claim 1, wherein the target molecule is selected from the group consisting of lipoproteins, lipoprotein fragments, glycoproteins, glycoprotein fragments, proteins, protein fragments, and polypeptides.

6. The method of claim 5, wherein the target molecule is selected from the group consisting of proteins, protein fragments, and polypeptides.

7. The method of claim 1, wherein the cell line is grown in media comprising $^2$H.

8. The method of claim 7, wherein the media comprises $^2$H$_2$O.

9. The method of claim 1, wherein the labeled precursor is labeled indole.

10. The method of claim 1, wherein the labeled precursor is labeled 4-hydroxyphenylpyruvate or labeled phenylpyruvate.

11. The method of claim 1, wherein the labeled precursor is labeled ornithine, labeled citrulline, or labeled argininosuccinate.

12. The method of claim 1, wherein the medium comprises a selective inhibitor of a single reaction step upstream of the labeled precursor in the biosynthesis of the amino acid.

13. The method of claim 1, wherein every occurrence of the particular amino acid in the target molecule is labeled.

14. A method for producing a target molecule wherein substantially every occurrence of a particular amino acid in the target molecule is labeled, wherein the amino acid is located at a functional site of the target molecule; and wherein substantially all occurrences of other amino acids are unlabeled, the method comprising:
    identifying an amino acid located at the functional site of the target molecule;
    providing a labeled precursor that selectively labels only the identified amino acid; and
    culturing a transformed cell line containing an expression vector comprising a polynucleotide encoding the target molecule in a medium comprising the labeled precursor to biosynthesis of the identified amino acid.

15. The method of claim 14, wherein the amino acid is tryptophan.

16. The method of claim 14, wherein the labeled precursor is labeled indole.

17. The method of claim 14, wherein the medium comprises a selective inhibitor of a single reaction step upstream of the labeled precursor in the biosynthesis of the amino acid.

18. A method for producing a target molecule wherein substantially every tryptophan residue in the target molecule is labeled, and wherein substantially all occurrences of other amino acids are unlabeled, the method comprising:
    providing a labeled precursor that selectively labels only tryptophan; and
    culturing a transformed cell line containing an expression vector comprising a polynucleotide encoding the target molecule in a medium comprising the labeled precursor to biosynthesis of tryptophan.

19. The method of claim 18, wherein the labeled precursor is labeled indole.

20. The method of claim 19, wherein the labeled precursor is 2-$^{13}$C indole.

21. The method of claim 19, wherein the labeled precursor is 4-$^{13}$C indole.

22. The method of claim 18, wherein the amino acid is labeled with a nucleus selected from the group consisting of $^1$H, $^{13}$C, $^{15}$N, and $^{19}$F.

23. The method of claim 22, wherein the nucleus is $^{19}$F.

24. The method of claim 18, wherein every occurrence of tryptophan in a functional site of the target molecule is labeled.

* * * * *